US009124986B2

(12) United States Patent
Pedersen

(10) Patent No.: US 9,124,986 B2
(45) Date of Patent: Sep. 1, 2015

(54) FEEDBACK CONTROL IN A LISTENING DEVICE

(75) Inventor: Michael Syskind Pedersen, Smørum (DK)

(73) Assignee: OTICON A/S, Smorum (DK)

( * ) Notice: Subject to any disclaimer, the term of this patent is extended or adjusted under 35 U.S.C. 154(b) by 531 days.

(21) Appl. No.: 13/533,293

(22) Filed: Jun. 26, 2012

(65) Prior Publication Data

US 2012/0328118 A1 Dec. 27, 2012

Related U.S. Application Data

(60) Provisional application No. 61/501,270, filed on Jun. 27, 2011.

(30) Foreign Application Priority Data

Jun. 27, 2011 (EP) .................................... 11171455

(51) Int. Cl.
*A61F 11/06* (2006.01)
*H04R 25/00* (2006.01)
*H04R 3/02* (2006.01)

(52) U.S. Cl.
CPC ................ *H04R 25/453* (2013.01); *H04R 3/02* (2013.01); *H04R 25/407* (2013.01); *H04R 25/554* (2013.01); *H04R 2225/41* (2013.01); *H04R 2225/61* (2013.01)

(58) Field of Classification Search
CPC ........ H04R 25/30; H04R 25/00; H04R 25/01; H04R 29/00; H04R 5/02; H04R 1/1041; H04R 1/1091; H04R 1/06; H04R 1/08; H04R 1/10; H04R 1/1016; H04R 1/1083; H04R 1/04; H04R 3/00; H04R 3/002; H04R 3/005; H04R 3/02; H04R 3/04; H04R 2225/025; H04R 2420/07; H04R 25/405; H04R 25/453; H04R 25/70; H04R 2410/05; H04R 2430/01; H04R 2499/11; H04L 27/01; H04B 7/17; H04B 15/00; H04B 3/20; H04B 3/23; H04M 1/00; G10K 11/16; G10K 11/175; G10K 11/1784; G10K 2210/1081; G10K 2210/30232; G10K 15/04; H03G 1/04; H03G 2201/103; H03G 3/20; H03G 3/348; H03G 5/16; H03G 5/165; H03F 3/181; G10L 21/0208; G10L 21/0224; G10L 21/0272; G10L 21/0332; G10L 21/034; G10L 15/00

USPC ............. 381/318, 320, 83, 93, 313, 108, 107, 381/97, 98, 100, 101, 102, 103, 328, 60, 56, 381/58, 321, 71.14, 71.6, 71.11, 71.12, 381/94.1–94.9, 73.1, 74, 92; 700/94; 708/300, 305, 322, 323; 455/63.1, 570; 379/406.01–406.16; 704/321.007, 704/E21.02; 327/551, 552, 553, 555, 560

See application file for complete search history.

(56) References Cited

U.S. PATENT DOCUMENTS 6,563,931 B1 * 5/2003 Soli et al. ...................... 381/318

(Continued)

FOREIGN PATENT DOCUMENTS

EP 0 581 262 A1 2/1994

(Continued)

OTHER PUBLICATIONS

Dyrlund et al., "Acoustic feedback margin improvements in hearing instruments using a prototype DFS (digital feedback suppression) system," Scand. Audiol., vol. 20, No. 1, pp. 49-53, 1991.

(Continued)

*Primary Examiner* — Leshui Zhang

(74) *Attorney, Agent, or Firm* — Birch, Stewart, Kolasch & Birch, LLP

(57) ABSTRACT

A listening device includes a) an input transducer; and b) an output transducer for converting a processed electric signal to an output sound; a forward signal path being defined there between and comprising c) a signal processing unit for processing an electric input signal or a signal derived therefrom and providing a processed output signal; d) a manually operable user interface located on the listening device allowing a user to control a function of the listening device; e) a feedback estimation system for estimating a feedback path from the output transducer to the input transducer, the feedback estimation system comprising e1) an adaptive filter having e11) a variable filter part and e12) an algorithm part comprising an adaptive algorithm.

20 Claims, 6 Drawing Sheets

(56) References Cited

U.S. PATENT DOCUMENTS

| | | | | |
|---|---|---|---|---|
| 2004/0013280 | A1* | 1/2004 | Niederdrank | 381/315 |
| 2007/0206824 | A1* | 9/2007 | Hellgren et al. | 381/313 |
| 2010/0329493 | A1 | 12/2010 | Arndt et al. | |

FOREIGN PATENT DOCUMENTS

| | | | |
|---|---|---|---|
| EP | 1460769 | A1 | 9/2004 |
| EP | 1981253 | A1 | 10/2008 |
| EP | 2 276 272 | A1 | 1/2011 |
| WO | WO 2005/091675 | A1 | 9/2005 |
| WO | WO 2009/135872 | A1 | 11/2009 |

OTHER PUBLICATIONS

Engebretson et al., "Properties of an adaptive feedback equalization algorithm," J. Rehabil. Res. Dev., vol. 30, No. 1, pp. 8-16, 1993.

* cited by examiner

FEEDBACK CONTROL IN A LISTENING DEVICE

CROSS REFERENCE TO RELATED APPLICATIONS

This nonprovisional application claims the benefit of patent application Ser. No. 11/171,455.6 filed in Europe on Jun. 27, 2011 and to U.S. Provisional Application No. 61/501,270 filed on Jun. 27, 2011. The entire contents of all of the above applications are hereby incorporated by reference.

TECHNICAL FIELD

The present application relates to feedback control in listening devices, e.g. hearing aids, subject to varying acoustic situations, and in which an output transducer is located sufficiently close to an input transducer of the device to cause feedback problems in certain situations. The disclosure relates specifically to a listening device adapted for being located in or at an ear of a user and comprising a manually operable user interface located on the listening device allowing a user to control an operating function of the listening device, and a feedback estimation system for estimating a feedback path from the output transducer to the input transducer.

The application furthermore relates to a method of operating a listening device, to a listening system, and to the use of a listening device.

The application further relates to a data processing system comprising a processor and program code means for causing the processor to perform at least some of the steps of the method and to a computer readable medium storing the program code means.

The disclosure may e.g. be useful in applications such as hearing aids, headsets, ear phones, active ear protection systems, etc.

BACKGROUND

The following account of the prior art relates to one of the areas of application of the present application, hearing aids.

Two different ways exist for changing programs/volume in a hearing aid. This is illustrated in FIG. 1. One way is to use a button at the hearing aid (FIG. 1*a*). The other way is to wirelessly change the program/volume through an external device such as a remote control (FIG. 1*b*). The difference is that the local acoustics around the hearing aid changes while the hand is near the ear (pressing an activation element on the hearing aid, FIG. 1*a*), but the local acoustics is unlikely to change in the other case where the hand is far from the hearing aid (on the remote control, FIG. 1*b*). When the local acoustics changes, the feedback path will change. This may result in howling.

EP 2 148 525 A1 describes a hearing instrument comprising a codebook of plausible feedback channel impulse responses (or any equivalent representation) and to make them available for selection and use by a signal processing unit in the appropriate listening situation, e.g. by storing them in a memory of the hearing instrument.

SUMMARY

When an actuation element on a listening device (e.g. a hearing aid) located at or behind the ear of a user is activated by the user's hand, it is expected that the hand will be removed as soon as the user has performed the intended action, e.g.

changed to a desired program or modified another setting, e.g. volume. In this situation, the feedback cancellation filter update algorithm is preferably adapted to not react on the acoustic changes caused by the manual operation of the activation element, because the acoustics is expected to change back to normal after a short while (where 'normal' typically will be the situation a (possibly short) while before the activation by the user of the actuation element, i.e. while the user's hand is approaching the hearing aid). When the program change (or other modification of a setting of the hearing aid) is done wirelessly, no local acoustic changes are expected, and the hearing aid feedback cancellation filter estimation should be adapted to its normal update routine. The present invention is related to the physical change of the local acoustic environment caused by a user's operation of an activation element on the listening device, rather than to the functional effect of the operation of the activation element in the listening device (e.g. a program change, a volume change, etc.).

An object of the present application is to provide an improved control mechanism for an adaptive filter.

Objects of the application are achieved by the invention described in the accompanying claims and as described in the following.

A Listening Device:

In an aspect of the present application, an object of the application is achieved by a listening device adapted for being located in or at an ear of a user and comprising

- an input transducer for converting an input sound to an electric input signal; and
- an output transducer for converting a processed electric signal to an output sound;
- a forward signal path being defined there between and comprising a signal processing unit for processing the electric input signal or a signal derived therefrom and providing a processed output signal;
- a manually operable user interface located at or on the listening device allowing a user to control a function of the listening device;
- a feedback estimation system for estimating a feedback path from the output transducer to the input transducer, the feedback estimation system comprising
  - an adaptive filter, the adaptive filter comprising
    - a variable filter part, and
    - an algorithm part comprising an adaptive algorithm,
  - the variable filter part being adapted for providing a transfer function to a filter input signal and providing a filtered output signal, the transfer function being controlled by filter coefficients determined in the algorithm part and transferred to the variable filter part, the feedback estimation system further comprising
  - an update control unit adapted for controlling the adaptive algorithm including the transfer of filter coefficients to the variable filter part,
- wherein the update control unit is adapted to monitor the manually operable user interface and to provide that an activation of the manually operable user interface is used for influencing the control of the adaptive algorithm.

This has the advantage of providing a scheme for handling the risk of howl during manual operation of a listening device adapted for being located at or in an ear of a user.

The term 'used for influencing the control of the adaptive algorithm' is in the present context taken to include the delay or omission or change of an action related to the adaptive algorithm that would otherwise have been performed in the listening device (had the user not activated the user interface).

The 'control of the adaptive algorithm' may e.g. relate to the timing of the calculation or re-calculation of filter coefficients (and/or to change of the adaptation rate of the adaptive algorithm) and/or to the transfer of filter coefficients from the algorithm part to the variable filter part.

In an embodiment, the listening device comprises an analysis path (in parallel to the forward signal path) comprising functional components for analyzing the input signal (e.g. determining a level, a modulation, a type of signal, an acoustic feedback estimate, etc.). In an embodiment, some or all signal processing of the analysis path and/or the signal path is conducted in the frequency domain. In an embodiment, some or all signal processing of the analysis path and/or the signal path is conducted in the time domain.

The listening device comprises an adaptive acoustic (and/or mechanical) feedback suppression system. Feedback suppression may be achieved by subtracting an estimate of the feedback signal within the listening device. It has been proposed to use a fixed coefficient linear time invariant filter for the feedback path estimate [Dyrlund, 1991]. This method proves to be effective if the feedback path is steady state and, therefore, does not alter over time. However, the feedback path of a listening device, e.g. a hearing aid, does vary over time and some kind of tracking ability is often preferred. Adaptive feedback cancellation has the ability to track feedback path changes over time. It is also based on a linear time invariant filter to estimate the feedback path but its filter weights are updated over time [Engebretson, 1993]. The filter update may be calculated using stochastic gradient algorithms, including some form of the popular Least Mean Square (LMS) or the Normalized LMS (NLMS) algorithms. They both have the property to minimize the error signal in the mean square sense with the NLMS additionally normalizing the filter update with respect to the squared Euclidean norm of some reference signal. Various aspects of adaptive filters are e.g. described in [Haykin].

In an embodiment, the manually operable user interface comprises a touch sensitive activation element. A touch sensitive element can e.g. comprise any switch element for selecting one of two or more options, e.g. a push button, a touch (sensitive) screen, a rotating wheel, a mechanical switch, a proximity sensor, etc.

In an embodiment, the listening device is adapted to provide that the feedback estimate is used to minimize or cancel feedback from the output transducer to the input transducer. In an embodiment, such adaptation is implemented by a combination unit for combining (e.g. a summation unit) the feedback path estimate with (e.g. subtracting from) an input signal, e.g. from a microphone or microphone system, of the listening device.

In an embodiment, the update control unit is adapted to control the timing of the calculation of filter coefficients and/or the transfer of filter coefficients to the variable filter part. In an embodiment, the update control unit comprises a timing unit that controls when new filter coefficients are to be calculated. In an embodiment, the update control unit comprises a timing unit that controls when newly calculated (or stored) filter coefficients are transferred to the variable filter part of the adaptive filter. When the manually operable user interface has been activated, the timing unit is adapted to influence the timing of the calculation of the filter coefficients and/or their transfer to the variable filter (based on the event of occurrence of the activation, and e.g. for a predefined time thereafter).

In an embodiment, the update control unit is adapted to inhibit or delay the calculation of filter coefficients and/or the transfer of filter coefficients to the variable filter part with a predefined time (after activation of the manually operable user interface). In an embodiment, the delay is adapted to be sufficiently large to allow the acoustic situation (including the feedback path from the output to the input transducer of the listening device) after user's activation of the manually operable user interface to be normalized, e.g. based on an estimated average value. In an embodiment, the delay is larger than 1 s, such as in the range from 1 s to 5 s, e.g. around 2 s. In an embodiment, the delay is larger than 5 s.

In an embodiment, the update control unit is adapted to modify the adaptation rate of the adaptive algorithm. In an embodiment, the adaptation rate is decreased when an activation of the manually operable user interface is detected in the listening device. In an embodiment, the adaptation rate is governed by a step size of the algorithm. In an embodiment, the step size of the algorithm is decreased when an activation of the manually operable user interface is detected. In an embodiment, the step size is set to zero when an activation of the manually operable user interface is detected and held at zero for a predefined (delay) time, where after it is returned to its original value or to a default value or to a value determined by the chosen program, if the activation of the manually operable user interface resulted in a program change. In an embodiment, the step size is frequency dependent, e.g. in that feedback estimation is performed fully or partially in the frequency domain. In an embodiment, the calculation of updated filter coefficients is performed in a number of frequency bands, whereas the filtering is performed in the time domain (cf. e.g. FIG. 3*c*).

In an embodiment, the listening device, e.g. the update control unit, comprises a memory wherein one or more default feedback path estimates is/are stored, and wherein the update control unit is adapted to select a default feedback path estimate from the memory and to transfer corresponding filter coefficients to the variable filter part when the manually operable user interface has been activated. In an embodiment, the default feedback path estimate comprises a channel impulse response, a complex-valued transfer function, or a set filter coefficients. In an embodiment, the one or more default feedback path estimates is/are determined and stored in the listening device in advance of its normal operation, e.g. in a fitting procedure. Alternatively or additionally, the one or more default feedback path estimates is/are determined during normal operation of the listening device. Different default feedback path estimates may be stored for different programs of the listening device corresponding to different listening situations (e.g. music, telephone, speech in noise, 'cocktail party', etc.). Preferably, changes to the feedback path estimate over time are monitored. During a stable time period, where little or no large changes to the feedback path estimate occurs, a value (e.g. an average value) of the feedback path estimate is stored in a memory of the listening device as a default feedback path estimate. In an embodiment, the 'stable' feedback path stored in memory is determined offline, e.g. during a fitting session of the listening device. In an embodiment, a number of the last determined feedback path estimates ($F_x(n)$, n being time) (e.g. corresponding filter coefficients) are stored in a memory. In an embodiment, a difference between the current feedback estimate ($F_x(n)$) and the immediately preceding feedback estimate ($F_x(n-1)$) is determined, e.g. as $|F_x(n)-(F_x(n-1)|^2$. In an embodiment, an average value (e.g. a running average) of the previous feedback path estimates is stored in the memory. In an embodiment, the older estimates are weighted less than the newer estimates, e.g. according to the recursive formula $F_{st,p}(n)=\alpha F_x(n-1)+(1-\alpha)F_x(n)$, where $F_{st,p}$ is the stored previous feedback estimate, n is a time index and $\alpha$ is a constant between 0 and 1.

The smaller the value of $\alpha$, the more weight on the latest values of the feedback estimate, and the larger the value of $\alpha$, the more weight on the historic values of the feedback estimate. In an embodiment, $\alpha$ is smaller than 0.5, such as smaller than 0.3, such as smaller than 0.2, such as in the range from 0.05 to 0.2. In an embodiment, a difference between the current feedback estimate ($F_x(n)$) and the stored feedback estimate ($F_{st}(n-1)$) is determined, e.g. as $|F_x(n)-(F_{st}(n-1)|^2$. In an embodiment, the current feedback estimate is an average over a number of the latest feedback estimates. In an embodiment, a difference between the current feedback estimate ($F_{st,c}$) and the preceding feedback estimate ($F_{st,p}$) is determined, e.g. as $|F_{st,c}-F_{st,p}|^2$. In an embodiment, one of the stored feedback path estimates is defined as a default feedback path estimate. This may be the case, if the difference between the current feedback estimate and the previous feedback estimate (e.g. the stored previous feedback estimate or the immediately preceding feedback estimate) is larger than a predetermined value (e.g. more than 50% larger or more than 100% larger) AND if the user interface is activated within a predetermined time of the last determined feedback path estimates (e.g. ≤0.1 s after, or ≤1 s after, or ≤5 s after). In an embodiment, after a user interface activation event, a choice between a number Nd of available stored default feedback path estimates is performed by choosing the feedback path estimate that provides the lowest prediction error, e.g. MIN $\epsilon[|y-Fd_x*u|^2]$, or, when normalized, MIN $\epsilon[|y-Fd_x*u|^2/|y|^2]$, where $\epsilon$ is the expected value operator, y is the current input signal (e.g. ER in FIG. 2, 3), $Fd_x$ is a default feedback estimate x, and u is the current output signal (e.g. REF in FIG. 2, 3), and where x is varied over the Nd available feedback paths.

Any operating parameter or function of the listening device may in principle be influenced by the manually operable user interface. In an embodiment, a function of the listening device that may be controlled via the manually operable user interface is a program shift or a volume change.

In an embodiment, the listening device is a portable device, e.g. a device comprising a local energy source, e.g. a battery, e.g. a rechargeable battery.

In an embodiment, the listening device comprises a hearing aid, a headset, an active ear protection device or a combination thereof.

In an embodiment, the listening device is adapted to provide a frequency dependent gain to compensate for a hearing loss of a user. In an embodiment, the signal processing unit is adapted for running algorithms for enhancing an input signal and providing a processed output signal. Various aspects of digital hearing aids are described in [Schaub; 2008].

In an embodiment, the output transducer comprises a receiver (speaker) for providing an acoustic signal to the user.

The listening device comprises an input transducer for converting an input sound to an electric input signal. In an embodiment, the listening device comprises a directional microphone system adapted to provide a resulting directional microphone characteristic of the system, e.g. for separating two or more acoustic sources in the local environment of the user wearing the listening device and/or for attenuating one acoustic source relative to another acoustic source. In an embodiment, the directional system is adapted to detect (such as adaptively detect) from which direction a particular part of the microphone signal originates. This can be achieved in various different ways as described in the prior art.

In an embodiment, the listening device comprises an antenna and transceiver circuitry for wirelessly receiving a direct electric input signal from another device, e.g. a communication device or another listening device. In an embodiment, the listening device comprises a (possibly standardized) electric interface (e.g. in the form of a connector) for receiving a wired direct electric input signal from another device, e.g. a communication device or another listening device.

In an embodiment, the communication between the listening device and the other device is in the base band (audio frequency range, e.g. between 0 and 20 kHz). Preferably, communication between the listening device and the other device is based on some sort of modulation at frequencies above 100 kHz. Preferably, frequencies used to establish communication between the listening device and the other device is below 50 GHz, e.g. located in a range from 50 MHz to 50 GHz.

In an embodiment, the listening device further comprises other relevant functionality for the application in question, e.g. compression, noise reduction, etc.

Use:

In an aspect, use of a listening device as described above, in the 'detailed description of embodiments' and in the claims, is moreover provided. In an embodiment, use is provided in a system comprising audio distribution, e.g. a system comprising a microphone and a loudspeaker in sufficiently close proximity of each other to cause feedback from the loudspeaker to the microphone during operation by a user. In an embodiment, use is provided in a system comprising one or more hearing instruments, headsets, ear phones, active ear protection systems, etc., e.g. in handsfree telephone systems, teleconferencing systems, public address systems, karaoke systems, classroom amplification systems, etc.

A method:

In an aspect, a method of operating a listening device, the listening device comprising

- an input transducer for converting an input sound to an electric input signal; and
- an output transducer for converting a processed electric signal to an output sound;
- a forward signal path being defined there between and comprising a signal processing unit for processing the electric input signal or a signal derived therefrom and providing a processed output signal;
- a manually operable user interface located at or on the listening device allowing a user to control a function of the listening device is furthermore provided by the present application.

The method comprises

- estimating a feedback path from the output transducer to the input transducer using an adaptive algorithm for determining filter coefficients for a variable filter;
- transferring filter coefficients to the variable filter thereby providing an estimated feedback path transfer function;
- monitoring the activation of the manually operable user interface;
- controlling the adaptive algorithm, including the transfer of filter coefficients to the variable filter, depending on the activation of the manually operable user interface.

It is intended that the structural features of the device described above, in the 'detailed description of embodiments' and in the claims can be combined with the method, when appropriately substituted by a corresponding process and vice versa. Embodiments of the method have the same advantages as the corresponding devices.

A Computer Readable Medium:

In an aspect, a tangible computer-readable medium storing a computer program comprising program code means for causing a data processing system to perform the steps of the method described above, in the 'detailed description of embodiments' and in the claims, when said computer program is executed on the data processing system is furthermore provided by the present application. In addition to being stored on a tangible medium such as diskettes, CD-ROM-, DVD-, or hard disk media, or any other machine readable medium, the computer program can also be transmitted via a transmission medium such as a wired or wireless link or a network, e.g. the Internet, and loaded into a data processing system for being executed at a location different from that of the tangible medium. In an embodiment, the data processing system comprises the signal processing unit of the listening device described above, in the 'detailed description of embodiments' and in the claims.

A Data Processing System:

In an aspect, a data processing system comprising a processor (e.g. the signal processing unit of the listening device described above, in the 'detailed description of embodiments' and in the claims) and program code means for causing the processor to perform the steps of the method described above, in the 'detailed description of embodiments' and in the claims is furthermore provided by the present application.

A Listening system:

In a further aspect, a listening system comprising a (first) listening device as described above, in the 'detailed description of embodiments', and in the claims, AND an auxiliary device is moreover provided. In an embodiment, the system comprises two or more auxiliary devices. In an embodiment, the listening system is portable.

In an embodiment, the system is adapted to establish a communication link between the listening device and the auxiliary device to provide that information (e.g. control and status signals, possibly audio signals) can be exchanged between them or forwarded from one to the other.

In an embodiment, the auxiliary device is an audio gateway device adapted for receiving a multitude of audio signals (e.g. from an entertainment device, e.g. a TV or a music player, a telephone apparatus, e.g. a mobile telephone, or a computer, e.g. a PC, a telecoil, a wireless microphone, etc.) and adapted for allowing a user to select and/or combine an appropriate one of the received audio signals (or combination of signals) for transmission to the listening device.

In an embodiment, the auxiliary device comprises a remote control function with a user interface adapted for allowing a user to modify settings of the first listening device.

In an embodiment, the auxiliary device is another (second) listening device. In an embodiment, the second listening device is a listening device as described above, in the 'detailed description of embodiments', and in the claims. In an embodiment, the listening system comprises two listening devices adapted to implement a binaural listening system, e.g. a binaural hearing aid system. In an embodiment, the listening system, comprises a binaural listening system, e.g. a hearing aid system, AND a further auxiliary device, e.g. an audio gateway device and/or a remote control device.

Further objects of the application are achieved by the embodiments defined in the dependent claims and in the detailed description of the invention.

As used herein, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element or intervening elements may be present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The disclosure will be explained more fully below in connection with a preferred embodiment and with reference to the drawings in which.

The figures are schematic and simplified for clarity, and they just show details which are essential to the understanding of the disclosure, while other details are left out.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

Figure 1A:
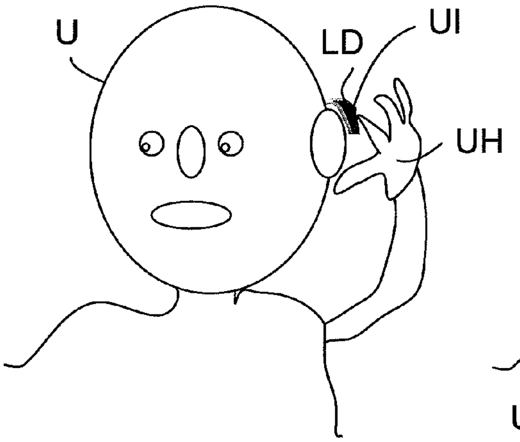
FIG. 1A PRIOR ART
FIG. 1 shows two user scenarios involving the changing of operational settings of a listening device.
Figure 1B:
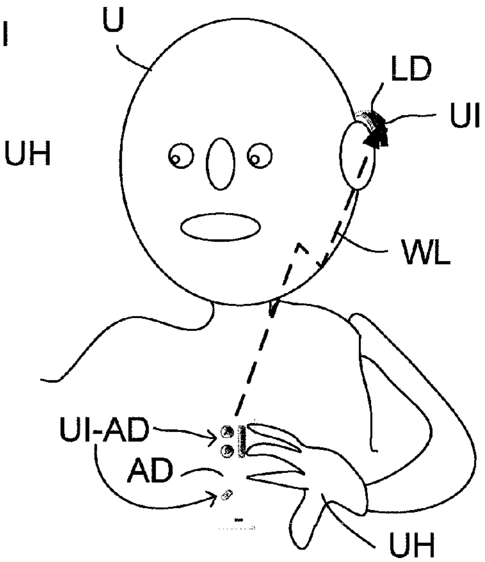
FIG. 1B PRIOR ART

FIG. 1 shows two user scenarios involving the changing of operational settings of a listening device. An operational condition, e.g. a program defining parameters of one or more processing algorithms, of a listening device (LD) may either be changed by a hand (UH) of a user (U) touching the user interface (UI) of the listening device (e.g. a push button of a hearing aid), as shown in FIG. 1*a*, or wirelessly using a user interface (UI-AD) of an external (auxiliary) device (AD), e.g. a remote control, adapted for transmitting the operational command corresponding to the user's activation of the user interface to the listening device via a wireless link (WL), as shown in FIG. 1*b*. In the scenario of FIG. 1*a*, the feedback path from the output transducer to the input transducer of the listening device changes (dramatically) and may result in howling, while the hand is near the ear to operate the user interface (UI) of the listening device. In the scenario of FIG. 1*b*, on the other hand, the feedback path is unlikely to change because the hand (UH) of the user (U) is not close to the listening device (but operates the user interface (UI-AD) of the auxiliary device (AD), e.g. a remote control, which is assumed to be sufficiently far away from the listening device (LD) to NOT influence the feedback path of the listening device).

Figure 2A:
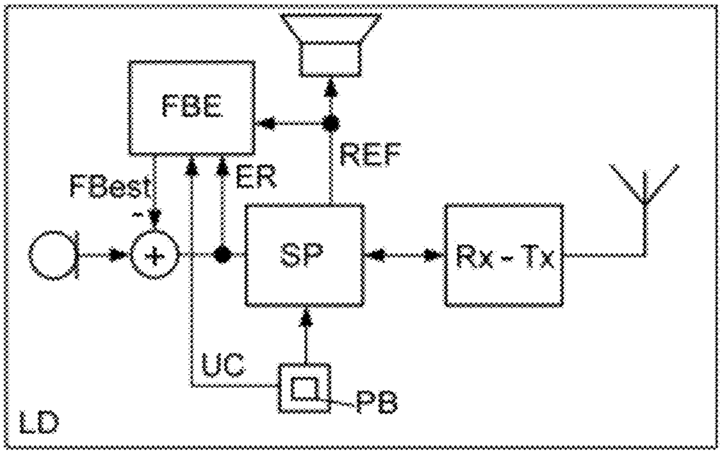
FIG. 2 shows an embodiment of a listening device (FIG. 2*a*), an embodiment of a feedback estimation system comprising an update control unit (FIG. 2*b*), and a binaural listening device system (FIG. 2*c*) according to the present disclosure.
Figure 2B:
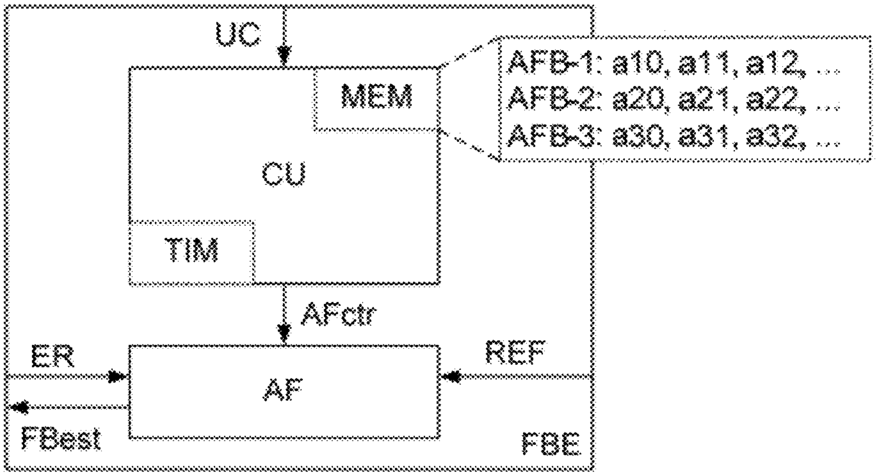
Figure 2C:
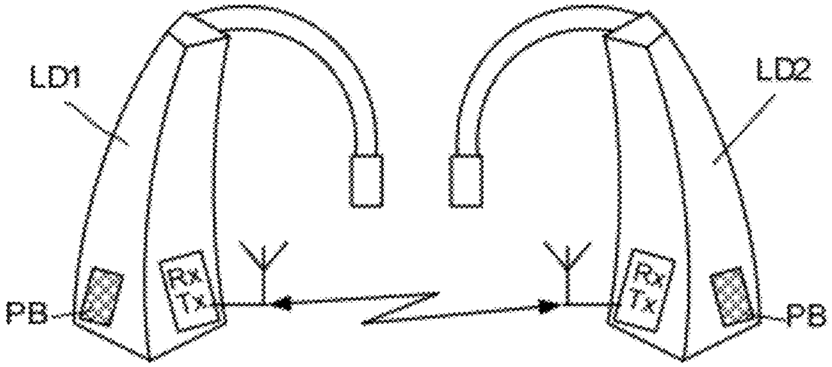

FIG. 2 shows an embodiment of a listening device (FIG. 2*a*), an embodiment of a feedback estimation system comprising an update control unit (FIG. 2*b*), and a binaural listening device system (FIG. 2*c*) according to the present disclosure.

FIG. 2*a* shows an embodiment of a listening device (LD) adapted for being located in or at an ear of a user and comprising a microphone for converting an input sound to an electric input signal and a (loud)speaker (also often termed 'a receiver') for converting a processed electric signal REF to an output sound, a forward signal path being defined there between and comprising a signal processing unit (SP) for processing the electric input signal or a signal derived therefrom ER and providing a processed, e.g. enhanced, electric (output) signal REF. The listening device further comprises a manually operable user interface located on the listening device, here in the form of push button PB, allowing a user to control a function of the listening device, e.g. its processing or a volume setting. The listening device further comprises a feedback estimation system (FBE) for estimating a feedback path from the speaker to the microphone (cf. signal FBest). As shown in FIG. 2*b*, the feedback estimation system (FBE) comprises adaptive filter (AF). The adaptive filter comprises a variable filter part and an algorithm part comprising an adaptive algorithm (cf. e.g. FIG. 3*b*), the variable filter part being adapted for providing a transfer function to a filter input signal REF and providing a filtered output signal FBest, the transfer function being controlled by filter coefficients determined in the algorithm part and transferred to the variable filter part. As shown in FIG. 2*b*, the feedback estimation system (FBE) further comprises an update control unit (CU) adapted for controlling the adaptive algorithm including the transfer of filter coefficients to the variable filter part of the adaptive filter (AF). The update control unit (CU) is further adapted to monitor the manually operable user interface (PB) and to provide that an activation of the manually operable user interface (resulting in signal UC) is used for influencing the control of the adaptive algorithm of the adaptive filter (AF). The embodiment of a listening device (LD) shown in FIG. 2*a* further comprises a combination unit (here sum unit '+') adapted for subtracting the estimate FBest of the feedback path from the electric input signal from the microphone thereby providing feedback corrected input signal ER (the feedback estimation unit (FBE) and the combination unit ('+') together implementing a feedback cancellation system). The embodiment of a listening device (LD) shown in FIG. 2*a* further comprises a wireless interface (indicated in FIG. 2*a* by antenna and transceiver circuitry (Rx-Tx)), e.g. to a remote control device and/or to a contra-lateral listening device of a binaural listening system (as illustrated in FIG. 2*c*). The (demodulated/decoded) signal from the wireless interface is connected to the signal processing unit (SP). The listening device may e.g. be adapted to receive an audio signal from an auxiliary device (e.g. a telephone or an audio gateway) via the wireless interface as an alternative or a supplement to the signal picked up by the microphone. Alternatively or additionally, the listening device may be adapted to receive control and/or status signals from an auxiliary device (e.g. a remote control device, cf. FIG. 4, or another listening device, cf. e.g. FIG. 2*c* or FIG. 5), such control and/or status signals being e.g. processed in the signal processing unit and used to control the listening device (e.g. change a volume setting or a program of the listening device and/or synchronize the operation of the listening device in question with that of a contra-lateral listening device of a binaural listening system). The listening device (LD) may comprise a BTE-part adapted for being located behind an ear or the user. In an embodiment, the user interface is located on the BTE-part (as e.g. illustrated in FIG. 1). The listening device (LD) may alternatively or additionally comprise an ITE-part adapted for being located in an ear or the user. In an embodiment, the user interface is located on the ITE-part.

FIG. 2*b* shows an embodiment of the feedback estimation system (FBE) of FIG. 2*a* comprising adaptive filter (AF) and control unit (CU) operationally (e.g. electrically) connected to each other. The control input UC from the user interface (PB) of the listening device indicating a user activation is connected to control unit (CU) where it is used to influence (possibly modify) the calculation and/or transfer of filter coefficients to the variable filter part of the adaptive filter (AF) as represented by signal AFctr in FIG. 2*b*. The adaptive filter (AF) receives inputs REF and ER from the output and input sides of the signal processing unit (SP), respectively, and provides feedback estimate output FBest. The embodiment of control unit (CU) of FIG. 2*b* comprises memory unit (MEM) and timing control unit (TIM). The memory unit comprises a memory wherein one or more default feedback path estimates is/are stored. The update control unit (CU) is adapted to select a default feedback path estimate from the memory and—in control of the timing control unit (TIM)—to (possibly extract and) transfer corresponding filter coefficients to the variable filter part of the adaptive filter (AF) when the manually operable user interface has been activated. The default feedback path estimate(s) AFB-i (i=1, 2, 3, . . . , Ns, Ns being the number of different default paths) stored in the memory unit (MEM) may e.g. comprise a channel impulse response, a complex-valued transfer function, and/or (as indicated in FIG. 2*b*) a number of sets of filter coefficients ai0, ai1, ai2, i=1, 2, 3, . . . Ns, where Ns is the number of different sets of filter coefficients stored in the memory, each e.g. being associated with a specific program Pi or other operational parameter (e.g. volume) of the listening device. In an embodiment, only one representation of a default feedback path, e.g. one set of default filter coefficients a0, a1, a2, . . . is stored. The timing control unit (TIM) is adapted to monitor the timing of the user's operation of the user interface (PB in FIG. 2*a*) AND to control the timing of the transfer of filter coefficients to the variable filter part of the adaptive filter (AF). The transferred filter coefficients may either be the ones calculated by the algorithm part of the adaptive filter (AF) OR those extracted (or read) from the memory unit (MEM). In an embodiment, a specific delay di is stored in the memory unit together with corresponding sets of filter coefficients ai0, ai1, ai2, . . . (or the relevant other representation of the default feedback path(s)). Such delay is used by the timing unit (TIM) to control the timing of the transfer of the corresponding default filter coefficients to the variable filter part of the adaptive filter instead of the ones (last) calculated by the algorithm part at a time equal to the (last) user activation time plus the delay time corresponding the action initiated by the user via the user interface (e.g. the selection of a particular program or a change of an(other) operational condition, e.g. a volume setting). The update control unit (CU) may also be adapted to modify a step size of the adaptive algorithm in dependence of a user's activation of the user interface, e.g. to decrease the step size p, e.g. to inhibit the adaptive algorithm (set the step size=0), for a certain amount of time (e.g. the delay time) relative to the (last) user activation time. After the delay time, the step size is set back to its value before the user activation or, preferably, to a default value μi, e.g. depending on the kind of action initiated by the user via the user interface. Such default step size values μi may e.g. stored together with other default settings di, aij referred to above.

FIG. 2*c* shows an application scenario of the listening device of FIG. 2*a* in a binaural listening device system, e.g. a binaural hearing aid system, here illustrated as two BTE (behind the ear) type listening devices (LD1, LD2) each comprising a user interface (PB) and a wireless interface (antenna and Rx Tx circuitry) adapted for establishing a wireless link between the two listening devices to (at least) allow the exchange of control and/or status signals between the two devices. In an embodiment, the control and/or status signals exchanged between the two listening devices are used to synchronize (selected) settings, e.g. volume or program selection, between the two devices. Preferably, the binaural listening system is adapted to only let the update control unit influence the control of the adaptive algorithm based on an activation of the manually operable user interface in the listening device where the activation by the user has occurred (i.e. NOT to include such action in the opposite listening device, i.e. NOT to synchronize the two listening devices in that respect). The listening devices (LD1, LD2) of FIG. 2*c* may e.g. comprise BTE-type hearing instruments of the receiver-in-the-ear (RITE) type comprising an ITE-part, where the receiver (speaker) is located at or in the ear canal of the user, whereas the microphone is located in the BTE part located behind the ear of the user. Alternatively a BTE-part or an ITE-part of each of the listening devices may comprise the speaker as well as the microphone.

Figure 3A:
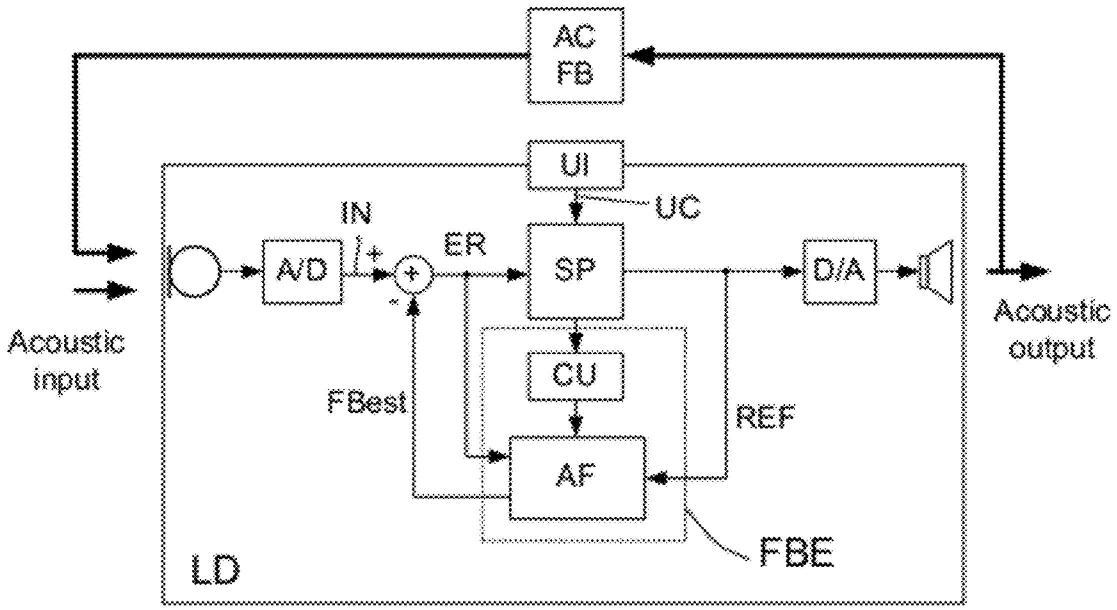
FIG. 3 shows three embodiments of a listening device according to the present disclosure.

FIG. 3 shows three embodiments of a listening device according to the present disclosure. FIG. 3*a* shows a listening device (LD) comprising a forward signal path from an input transducer to an output transducer, the forward signal path comprising a signal processing unit (SP) for applying a frequency dependent gain to the signal picked up by the microphone and providing an enhanced signal (REF) to the speaker. The input transducer (here a microphone) is adapted for converting an acoustic input signal (Acoustic input) to an electric input signal and may comprise an analogue-to-digital (A/D) converter (here shown as a separate unit) for digitizing the analogue signal from the input transducer and providing a digitized input signal (IN). The input transducer may comprise a number of microphones allowing a directional signal to be determined, e.g. as a weighted combination of individual microphone signals. The output transducer (here a speaker) is adapted for converting a processed electric signal to an acoustic output signal (Acoustic output) and may comprise a digital-to-analogue (D/A) converter (here shown as a separate unit) for converting a digital processed electric signal (REF) to an analogue signal fed to the output transducer. A feedback cancellation system for reducing or cancelling acoustic feedback (symbolized by feedback path (AC FB) from output to input transducer of the listening device) comprises 1) a feedback estimation unit (FBE) for providing an estimate FBest of the feedback path (here from the input to the D/A-converter to the output of the ND-converter) and 2) a combination unit ('+'). The feedback estimate signal FBest is subtracted from the input signal (IN) in combination unit ('+') providing feedback corrected signal (ER), which form an input to the signal processing unit (SP) and is subject to relevant processing therein (e.g. adapted to adjust the signal to the impaired hearing of a user). The feedback estimation unit (FBE) comprises an adaptive filter (AF), which is controlled by update control unit (CU). The adaptive filter (AF) provides feedback estimate FBest based on input signals REF and ER from the signal processing unit (SP) and combination unit ('+'), respectively. The listening device comprises a manually operable user interface (UI), which is electrically connected to the signal processing unit (SP) via control signal UC allowing the signal processing unit to apply the intended user input, e.g. a program shift, to the listening device. The output UC from the user interface is further used in the update control unit (CU) to influence the update of the transfer function of the adaptive filter. In the embodiments of FIG. 3, information about the activation of the user interface, e.g. in the form of control signal UC or a processed version thereof, is forwarded to the update control unit (CU) via the signal processing unit (SP). In practice, the update control unit (CU) (and the adaptive filter (AF)) may fully or partially be integrated with the signal processing unit (SP).

Figure 3B:
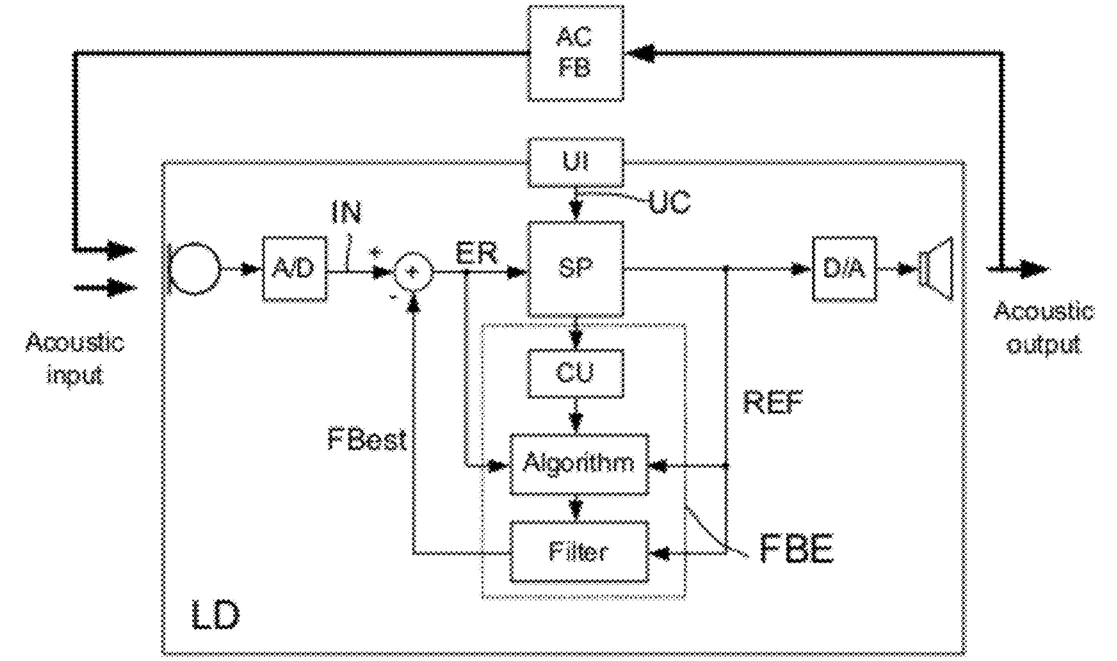

As shown in FIG. 3*b*, the adaptive filter (AF in FIG. 3*a*) comprises a variable filter part (Filter) and an algorithm part (Algorithm). The variable filter part provides a specific transfer function to an input signal (REF) in the form of a filtered output signal (FBest) based on update settings (filter coefficients) received from the algorithm part at specific points in time. The algorithm part comprises a prediction error algorithm, e.g. an LMS (Least Means Squared) algorithm, in order to predict and cancel the part of the microphone signal that is caused by the feedback path. The prediction error algorithm uses a reference signal (here the output signal REF) together with a signal originating from the microphone signal (here the feedback corrected input signal ER) to find the setting of the adaptive filter that minimizes the prediction error, when the reference signal REF is applied to the adaptive filter (i.e. to minimize a statistical deviation measure of ER(n) (e.g. $\epsilon[|ER(n)|^2]$, where $\epsilon$ is the expected value operator) and ER(n) is the digitized feedback corrected signal ER at time instance n). The adaptation rate of the adaptive filter is e.g. determined by a step size of the prediction error algorithm. The timing of the transfer of updated filter coefficients from the algorithm part to the variable filter part is controlled by update control unit (CU). The timing of the update (e.g. its specific point in time, and/or its update frequency) may be influenced by various properties of the signal of the forward signal path, e.g. the autocorrelation of the signal. Such properties may be detected by various sensors of the listening device, e.g. a feedback detector for detecting whether a given frequency component is likely to be due to feedback or to be inherent in the input signal (e.g. music). The timing of the update may further be influenced by a user's manual activation of the user interface (UI) located on the listening device, e.g. by inhibiting the transfer of updated filter coefficients from the algorithm part to the variable filter part of the adaptive filter for a predetermined time after such user operation, under the assumption that the feedback path is—temporarily—changed and will be re-established at its previous level within such predetermined delay period (e.g. between 1 and 5 s) after the activation. In case of several subsequent manual activations of the user interface, the delay period in question should be applied relative to the last activation (assuming that each subsequent activation occurs within such predetermined delay period of the previous activation). During a period of no manual activation of the user interface (UI), the transfer of filter coefficients determined by the algorithm part of the variable filter to the variable filter part is controlled in a normal fashion, e.g. every time a new set of coefficients has been calculated as governed by the step size of the algorithm or by any other predetermined or adaptively determined update frequency. In an embodiment, a set of filter coefficients for the last update (e.g. at time instant n−1, or an average, e.g. a weighted average, of a number of previous updates, e.g. the n−1 last) is stored in a memory of the listening device. In an embodiment, the update control unit is adapted to determine a value of the feedback estimate (or a prediction error of the feedback path) at the current time instant (e.g. time instant n) and compare it with the stored one from the previous time instant (e.g. n−1) (or from an average of a number of previous time instants). In an embodiment, the update control unit is adapted to calculate a difference between the prediction error of the feedback path at the current time instant (e.g. time instant n) and the prediction error of the feedback path at the previous time instant (e.g. n−1), and to store the previous set of filter coefficients (corresponding to time instant n−1) in the memory, if the calculated difference is larger than a predefined amount (indicating that the feedback path has changed substantially from one time instant to the next). In case that the change in the feedback path is immediately succeeded or preceded (e.g. within 1-5 s) by a user's operation of the user interface on the listening device, it is assumed that the change in the feedback path is due to such (approaching, ongoing or ending) user operation. The filter coefficients may then be read from the memory and used to represent an initial (default) feedback estimate when normal operation is resumed, e.g. when a predetermined delay time has elapsed since the activation of the user interface.

Figure 3C:
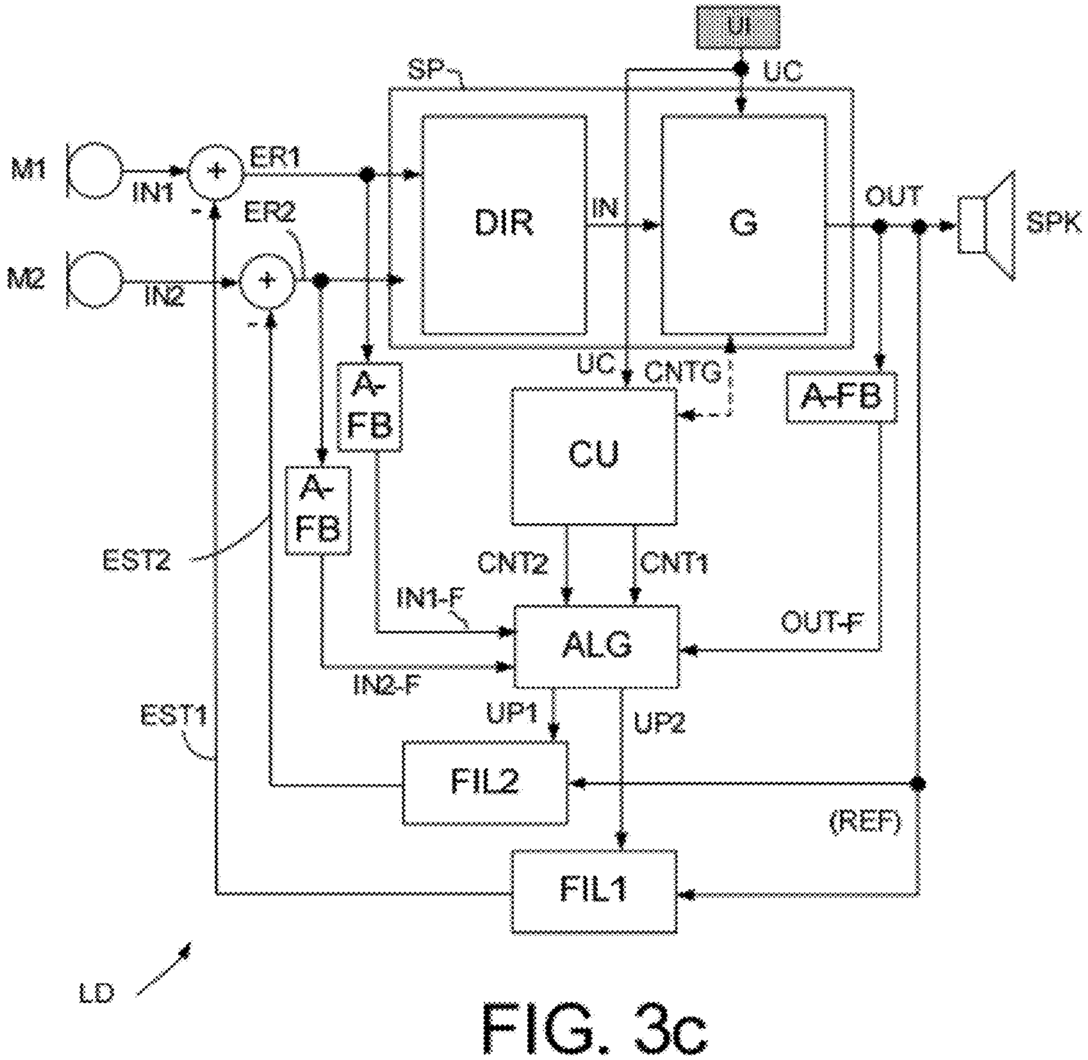

FIG. 3*c* shows an embodiment of a listening device according to the present disclosure wherein the calculation of updated filter coefficients is performed in a number of frequency bands, whereas the filtering providing the feedback path estimate signal is performed in the time domain. The embodiment of a listening device (LD) of FIG. 3*c* is similar to the one illustrated in FIG. 3*b*. A difference is that the embodiment of FIG. 3*c*-instead of a single (e.g. omni-directional) microphone—comprises a microphone system comprising two microphones (M1, M2) providing input microphone signals IN1, IN2 and a directional algorithm (DIR) providing a weighted combination of the two input microphone signals in the form of directional (or omni-directional) signal IN, which is fed to gain block (G) for applying a frequency dependent gain to the input signal and providing a processed output signal OUT, which is fed to the speaker unit (SPK). Units DIR and G correspond to signal processing unit (SP) of FIGS. 3*a* and 3*b*. The embodiment of a listening device (LD) of FIG. 3*c* comprises two feedback estimation paths, one for each of the feedback paths from speaker SPK to microphones M1 and M2, respectively. A feedback estimate (EST1, EST2) for each feedback path is subtracted from the respective input signals IN1, IN2 from microphones (M1, M2) in respective subtraction units ('+'). The outputs of the subtraction units ER1, ER2 representing respective feedback corrected input signals are fed to the signal processing unit (SP), here to the directional unit (DIR). Each feedback estimation path comprises an adaptive filter (comprising a variable filter part (FIL1, FIL2) for filtering a (time domain) input signal (OUT or reference signal (REF)) and providing a filtered (time domain) output signal (EST1, EST2, respectively) providing an estimate of the respective feedback paths based on filter coefficients received from an algorithm part (ALG). The algorithm part for performing calculation of update filter coefficients (for both filters, symbolically assembled in unit ALG) receives inputs based on the output signal OUT and the feedback corrected input signals ER1, ER2. These inputs are, however, split into a number of frequency bands in respective analysis filter banks (A-FB) to provide respective band-split signals OUT-F, IN1-F, and IN2-F. The calculation of update information to the filter(s) based on individual (possibly different) adaptation rates of the adaptation algorithm in each frequency band is performed and controlled (in relation to inputs from a user interface (UI) via signal UC) as described previously in connection with the update control unit (CU). The update control unit (CU) provides respective update control signals CNT1, CNT2 to the algorithm unit (ALG) to control the respective adaptive algorithms for the corresponding adaptive filters. Time domain filter coefficients UP1, UP2 for the variable filter parts (FIL1, FIL2) are determined by transforming update information from the individual frequency bands in respective synthesis filter banks (included in the algorithm unit ALG). This approach has the advantage of allowing a different adaptation rate in different frequency bands. A further advantage is that the delay of the adaptive filter is relatively low.

Figure 4:
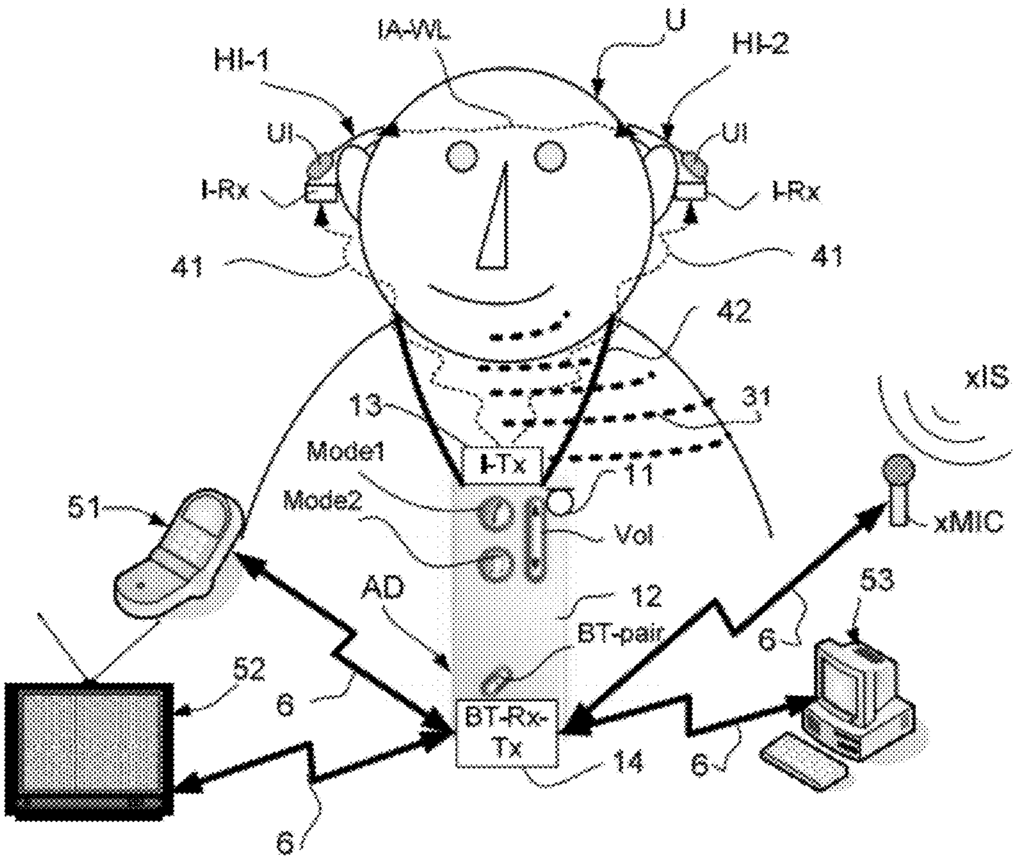
FIG. 4 shows an embodiment of a listening system comprising a pair of listening devices and an audio gateway, the system being adapted for establishing communication between the devices.

FIG. 4 shows an embodiment of a listening system comprising a pair of listening devices and an audio gateway, the system being adapted for establishing communication between the devices. FIG. 4 shows an application scenario of an embodiment of a portable listening system according to the present invention comprising a pair of listening devices, in the form or a binaural hearing aid system (HI-1, HI-2), and an auxiliary device (AD), wherein the auxiliary device comprises an audio gateway device including remote control functions for the listening devices (program shift, volume control, link establishment, etc.). The audio gateway device (AD) is adapted for receiving a multitude of audio signals (here shown from an entertainment device, e.g. a TV (52), a telephone apparatus, e.g. a mobile telephone (51), a computer, e.g. a PC (53), and an external microphone (xMIC) for picking up sounds xIS from the environment, e.g. the voice of another person). In the embodiment of FIG. 4, the microphone (11) of the audio gateway device (AD) is adapted for picking up the user's own voice (31) and capable of being connected to one or more of the external audio sources (e.g. telephone 51, or PC 53) via wireless links 6, here in the form of digital transmission links according to the Bluetooth standard as indicated by the Bluetooth transceiver (14) (BT-Tx-Rx) in the audio gateway device (AD). The audio sources and the audio gateway device may be paired using the button BT-pair. The wireless links may alternatively be implemented in any other convenient wireless and/or wired manner, and according to any appropriate modulation type or transmission standard, possibly different for different audio sources. Other audio sources than the ones shown in FIG. 4 may be connectable to the audio gateway, e.g. an audio delivery device (such as a music player), a telecoil, an FM-microphone or the like. The audio gateway device (AD) further comprises a selector/combiner unit (not shown in FIG. 4) adapted for selecting and/or combining an appropriate signal or combination of signals (from the audio sources connected to the audio gateway device at a given time) for transmission to the hearing instruments (HI-1, HI-2). The intended mode of operation of the listening system can be selected by the user via mode selection buttons Mode1 and Mode2. Here Mode1 indicates e.g. a telephone conversation mode (where the audio signal from a currently actively paired telephone is selected) and Mode2 indicates e.g. an entertainment device mode (where the audio signal from a currently actively paired entertainment device, e.g. the TV or a music player, is selected). The user and/or the particular selected mode may determine the signals to be selected/combined in the selector/combiner unit for transmission to the hearing instruments. The audio gateway device (AD) further has the function of a remote control of the hearing instruments, e.g. for changing program or operating parameters (e.g. volume, cf. Vol-button) in the hearing instruments (HI-1, HI-2). The hearing instruments (HI-1, HI-2) comprise a manually operable user interface (UI), whereby the user is allowed to change operating conditions of each individual (or both) hearing instruments by manual operation of the user interface (e.g. a push button), e.g. for changing program or operating parameters (e.g. volume. The system is preferably adapted to provide that the change of program or operating parameters of the listening device only activates the special control of the feedback estimation unit (cf. FIG. 2, 3), if such changes are initiated on the user interface (UI) of one of the listening devices (HI-1, HI-2), and only in the listening device, where the manual activation has actually occurred. In other words, a listening device is adapted to differentiate between control signals received from a remote control (or other auxiliary device) and (equivalent) control signals receive via the user interface on the listening device in question.

The listening devices, here hearing instruments (HI-1, HI-2), are shown as devices mounted at the left and right ears of a user (U). The hearing instruments of the system of FIG. 4 each comprise a wireless transceiver, here indicated to be based on inductive communication (I-Rx). The transceiver (at least) comprises an inductive receiver (i.e. an inductive coil, which is inductively coupled to a corresponding coil in a transceiver (I-Tx) of the audio gateway device (AD)), which is adapted to receive the audio signal from the audio gateway device (either as a baseband signal or as a modulated (analogue or digital) signal, and in the latter case to extract the audio signal from the modulated signal). The inductive links 41 between the audio gateway device and each of the hearing instruments are indicated to be one-way, but may alternatively be two-way (e.g. to be able to exchange control signals between transmitting (AD) and receiving (HI-1, HI-2) device, e.g. to agree on an appropriate transmission channel). Alternatively or additionally, the listening device (and/or the audio gateway device) may be adapted to receive an audio signal from a telecoil (T-coil) in the environment of the device and/or from an FM-transmitter (e.g. forming part of an external microphone).

The audio gateway device (AD) is shown to be carried around the neck of the user (U) in a neck-strap 42. The neck-strap 42 may have the combined function of a carrying strap and a loop antenna into which the audio signal from the audio gateway device is fed for better inductive coupling to the inductive transceiver of the listening device. An audio selection device, which may be modified and used according to the present invention is e.g. described in EP 1 460 769 A1, EP 1 981 253 A1 and in WO 2009/135872 A1.

The hearing instruments (HI-1, HI-2) are further adapted to establish an interaural wireless link (IA-WL) (e.g. an inductive link) between them, at least for exchanging status or control signals between them.

Figure 5:
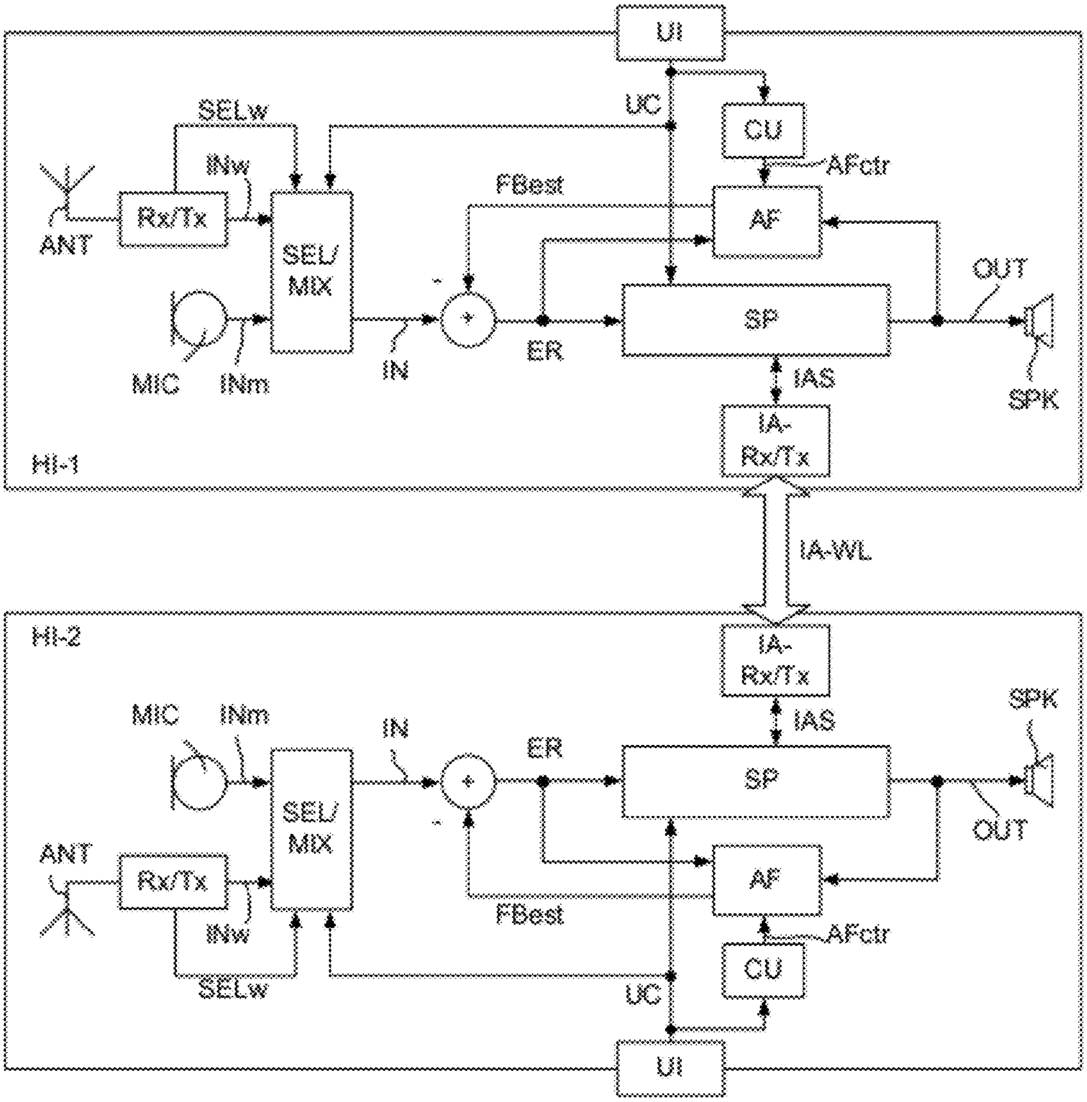
FIG. 5 shows an embodiment of a binaural hearing aid system comprising first and second hearing instruments.

FIG. 5 shows an embodiment of a binaural hearing aid system comprising first and second hearing instruments. The binaural hearing aid system comprises first and second hearing instruments (HI-1, HI-2) adapted for being located at or in left and right ears of a user (cf. e.g. FIG. 4). The hearing instruments are adapted for exchanging information between them via a wireless communication link, e.g. a specific inter-aural (IA) wireless link (IA-WL). The two hearing instruments (HI-1, HI-2) are adapted to allow the exchange of status signals, e.g. including the transmission of characteristics of the input signal received by a device at a particular ear to the device at the other ear. To establish the inter-aural link, each hearing instrument comprises antenna and transceiver circuitry (here indicated by block IA-Rx/Tx). Each hearing instrument HI-1 and HI-2 comprise a forward signal path comprising a microphone (M/C) a signal processing unit (SP) and a speaker (SPK), and a feedback cancellation system comprising a feedback estimation unit (comprising adaptive filter (AF) and update control unit (CU), the update control unit (CU) receiving control signal UC from the user interface (UI) and controlling the adaptive filter (AF) via control signal AFctr) and combination unit (Y) as described in connection with FIG. 2 or 3. In the binaural hearing aid system of FIG. 5, a control signal IAS generated by a control part of the signal processing unit (SP) of one of the hearing instruments (e.g. HI-1) is transmitted to the other hearing instrument (e.g. HI-2) and/or vice versa. The control signals from the local and the opposite device are e.g. in some cases used together to influence a decision or a parameter setting in the local device. The control signals may e.g. comprise information that enhances system quality to a user, e.g. improve signal processing. The control signals may e.g. comprise directional information or information relating to a classification of the current acoustic environment of the user wearing the hearing instruments, etc. Preferably, however, the binaural hearing aid system is adapted NOT to synchronize the two hearing instruments as regards the control of the adaptive algorithm based on an activation of the manually operable user interface in a specific hearing instrument (i.e. the system is adapted to initiate such action only in the hearing instrument where a manual activation of the user interface has occurred).

In an embodiment, the hearing instruments (HI-1, HI-2) each comprise wireless transceivers (ANT, Rx/Tx) for receiving a wireless signal (e.g. comprising an audio signal and/or control signals) from an auxiliary device, e.g. an audio gateway device and/or a remote control device. The hearing instruments each comprise a selector/mixer unit (SEL/MIX) for selecting either of the input audio signal INm from the microphone or the input signal INw from the wireless receiver unit (ANT, Rx/Tx) or a mixture thereof, providing as an output a resulting input signal IN. In an embodiment, the selector/mixer unit can be controlled by the user via the user interface (UI), cf. control signal UC and/or via the wirelessly received input signal (such input signal e.g. comprising a corresponding control signal or a mixture of audio and control signals). In the embodiment of FIG. 5, an extraction of a selector/mixer control signal SELw is performed in the wireless receiver unit (ANT, Rx/Tx) and fed to the selector/mixer unit (SEL/MIX).

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims.

REFERENCES

[Schaub; 2008] Arthur Schaub, Digital hearing Aids, Thieme Medical. Pub., 2008

[Haykin] S. Haykin, Adaptive filter theory (Fourth Edition), Prentice Hall, 2001.

[Dyrlund, 1991] O. Dyrlund, N. Bisgaard, "Acoustic feedback margin improvements in hearing instruments using a prototype DFS (digital feedback suppression) system", Scand. Audiol., 20(1), pp. 49-53, 1991

[Engebretson, 1993] A. Engebretson, M. French-St. George, "Properties of an adaptive feedback equalization algorithm", J. Rehabil. Res. Dev., 30(1), pp. 8-16, 1993

EP 1 460 769 A1 (PHONAK)

EP 1 981 253 A1 (OTICON)

WO 2009/135872 A1 (OTICON)

The invention claimed is:

1. A listening device adapted for being located in or at an ear of a user and comprising:

an input transducer for converting an input sound to an electric input signal;

an output transducer for converting a processed electric signal to an output sound;

a forward signal path being defined between the input transducer and the output transducer and comprising a signal processing unit for processing the electric input signal or a signal derived from the electric input signal and providing a processed output signal;

a manually operable user interface located on the listening device allowing a user to control a function of the listening device; and a feedback estimation system for estimating a feedback path estimate from the output transducer to the input transducer, the feedback estimation system comprising an adaptive filter, the adaptive filter comprising a variable filter part and an algorithm part comprising an adaptive algorithm, the variable filter part being adapted for providing a transfer function to a filter input signal and providing a filtered output signal, the transfer function being controlled by filter coefficients determined in the algorithm part and transferred to the variable filter part, the feedback estimation system further comprising an update control unit adapted for controlling the adaptive algorithm including a transfer of the filter coefficients to the variable filter part, wherein the update control unit is adapted to monitor the manually operable user interface and to provide that an activation of the manually operable user interface is used for influencing the control of the adaptive algorithm, wherein the update control unit comprises a timing unit that controls when newly calculated or stored filter coefficients are transferred to the variable filter part of the adaptive filter, and wherein the timing unit is adapted to influence timing of a calculation of the filter coefficients and/or the transfer of the filter coefficients to the variable filter, when the manually operable user interface has been activated.

2. The listening device according to claim 1, wherein the manually operable user interface comprises a touch sensitive element.

3. The listening device according to claim 1 adapted to provide that the feedback path estimate is used to minimize or cancel feedback from the output transducer to the input transducer.

4. The listening device according to claim 1, wherein the update control unit is adapted to monitor changes to the feedback path estimate over time.

5. The listening device according to claim 1, wherein the update control unit is adapted to inhibit or delay the calculation of the filter coefficients and/or the transfer of the filter coefficients to the variable filter part with a predefined time.

6. The listening device according to claim 1, wherein the update control unit is adapted to modify an adaptation rate of the adaptive algorithm.

7. The listening device according to claim 1, further comprising: a memory wherein one or more default feedback path estimates is/are stored, and wherein the update control unit is adapted to select a default feedback path estimate from the memory and to transfer corresponding filter coefficients to the variable filter part when the manually operable user interface has been activated.

8. The listening device according to claim 7, wherein the default feedback path estimate comprises a channel impulse response, a complex-valued transfer function, or a set of filter coefficients.

9. The listening device according to claim 7, wherein the one or more default feedback path estimates is/are determined and stored in the listening device in advance of its normal operation.

10. The listening device according to claim 7, wherein the one or more default feedback path estimates is/are determined during normal operation of the listening device.

11. The listening device according to claim 7 adapted to provide that a choice between stored default feedback paths is performed by choosing the feedback path estimate that provides a lowest prediction error MIN $E[|y-Fd_x*u|^2]$, where E is an expected value operator, y is a current input signal, $Fd_x$ is a default feedback estimate x, and u is a current output signal, and where x is varied over available feedback paths.

12. The listening device according to claim 1, wherein a function of the listening device that may be controlled via the manually operable user interface is a program shift or a volume change.

13. The listening device according to claim 1 adapted to store a number of instances of a last determined feedback path estimate $F_x(n)$, n being time, in a memory.

14. The listening device according to claim 13 adapted to determine a difference between a current feedback estimate $F_x(n)$ and an immediately preceding feedback estimate $(F_x(n-1))$.

15. The listening device according to claim 14 adapted to select one of the stored default feedback path estimates as the current feedback path estimate, if the difference between the current feedback estimate and a previous feedback estimate is larger than a predetermined value AND if the manually operable user interface is activated within a predetermined time of a last determined feedback path estimates.

16. A listening system, comprising:

a first listening device that is the listening device according to claim 1; and one or more auxiliary devices, wherein the listening system is adapted to establish a communication link between the first listening device and an auxiliary device of the one or more auxiliary devices to provide that information can be exchanged or forwarded from one to the other.

17. The listening system according to claim 16, wherein the auxiliary device comprises an audio gateway function adapted for receiving a multitude of audio signals and for allowing a user to select and/or combine an appropriate one of the multitude of audio signals or a combination of the multitude of audio signals for transmission to the listening device.

18. The listening system according to claim 16, wherein the auxiliary device comprises a second listening device.

19. A method of operating a listening device, the listening device comprising an input transducer for converting an input sound to an electric input signal; and an output transducer for converting a processed electric signal to an output sound;

a forward signal path being defined between the input transducer and the output transducer and comprising a signal processing unit for processing the electric input signal or a signal derived from the electric input signal and providing a processed output signal;

a manually operable user interface located on the listening device allowing a user to control a function of the listening device, the method comprising:

estimating a feedback path from the output transducer to the input transducer using an adaptive algorithm for determining filter coefficients for a variable filter;

transferring the filter coefficients to the variable filter thereby providing an estimated feedback path transfer function;

monitoring an activation of the manually operable user interface with an update control unit; and controlling the adaptive algorithm with the update control unit, the controlling including controlling the transferring of the filter coefficients to the variable filter, and controlling timing of the calculation of the filter coefficients and/or the timing of a transfer of the filter coefficients to the variable filter part with a timing unit of the update control unit, depending on the activation of the manually operable user interface.

20. A non-transitory tangible computer-readable medium storing a computer program comprising program code means for causing a data processing system to perform at the steps of the method of claim 19, when said computer program is executed on the data processing system.

* * * * *